United States Patent [19]

Lysenko et al.

[11] Patent Number: 4,468,354

[45] Date of Patent: Aug. 28, 1984

[54] CONTINUOUS PROCESS FOR PREPARING 5-OXO-2,4-DICHLORO-4-SUBSTITUTED PENTANENITRILES

[75] Inventors: Zenon Lysenko; Richard G. Pews, both of Midland, Mich.

[73] Assignee: The Dow Chemical Company, Midland, Mich.

[21] Appl. No.: 466,451

[22] Filed: Feb. 15, 1983

[51] Int. Cl.$^3$ .................. C07C 121/34; C07C 121/76
[52] U.S. Cl. ................................ 260/465.7; 260/464; 260/465 G; 546/250
[58] Field of Search ................ 260/465.7, 465 G, 464; 546/250

[56] References Cited

U.S. PATENT DOCUMENTS 4,245,098  1/1981  Steiner et al. ...................... 546/250

FOREIGN PATENT DOCUMENTS 0046735  8/1981  European Pat. Off. .

Primary Examiner—Dolph H. Torrence

[57] ABSTRACT

A continuous process for preparing 5-oxo-2,4-dichloro-4-alkyl or aryl pentanenitriles, e.g., 5-oxo-2,4-dichloro-4-methylpentanenitrile-1 by reacting an α,α-dichloroaldehyde with an acrylonitrile in a coil reactor.

7 Claims, No Drawings

CONTINUOUS PROCESS FOR PREPARING 5-OXO-2,4-DICHLORO-4-SUBSTITUTED PENTANENITRILES

BACKGROUND OF THE INVENTION

A process for making 2,3,5-trichloropyridine and 2,4,4-trichloro-4-formylbutyronitrile from trichloroacetaldehyde and acrylonitrile is described in European patent application No. 12117.

The preparation of 2,2-dichloroaldehydes is described by DeBuyck et al, Bull. Soc. Chem. Belg. 89, 441 (1980) and in copending application Ser. No. 487,476, filed Apr. 22, 1983.

European patent application No. 46735 describes and claims a process for the preparation of methyl-, trichloromethyl- or trifluoromethyl substituted chloropyridines by cyclizing compounds having the formula

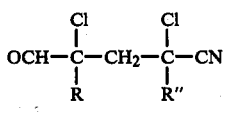

wherein R is chloro and R″ is methyl or trifluoromethyl, R is methyl, trichloromethyl or trifluoromethyl and R″ is hydrogen or R and R″ are both methyl.

SUMMARY OF THE INVENTION

This invention provides a continuous process for making compounds having the formula

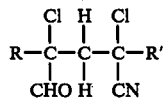

where R and R′ are individually hydrogen or a straight or branched chain aliphatic radical having 1 to 8 carbon atoms, phenyl, benzyl, cyclohexyl, trichloromethyl or trifluoromethyl which comprises reacting an aldehyde having the formula

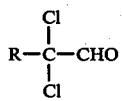

where R is as above-defined, with an acrylonitrile compound having the formula

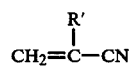

where R′ is as defined above in the presence of a transition metal catalyst in a continuous reactor, the interior surface of which contains no more than a minor percentage of iron. The desired products may thereafter be separated from the reaction medium by conventional means.

DETAILED DESCRIPTION OF THE INVENTION

The process of this invention is advantageously carried out at a temperature of from 90° to 220° C. in the presence of a transition metal catalyst. Preferably, the reaction is carried out at a temperature of from 185° to 200° C. in the presence of a catalyst. Advantageously, the mole ratio of dichloroaldehyde to acrylonitrile compound is from 1:1 to 1:3, preferably 1:2.

The catalyst employed is advantageously a transition metal catalyst such as, for example, powders, salts and/or organic complexes of rhodium, palladium, copper, ruthenium, cobalt and mixtures thereof. Preferred catalysts are copper powder, copper bronze and cuprous and cupric chloride and bromide, as well as mixtures thereof. Co-catalysts such as, for example, organic phosphines, amines and alcohols may be employed if desired. The catalysts are advantageously employed in an amount of from 0.01 to 10 mole percent, preferably 0.1 to 5 mole percent, based on the aldehyde used.

The interior reactor surface is preferably a tantalum surface, although surfaces having a high nickel content, for example a Monel or Hastalloy surface, can be employed with advantage.

The invention is further illustrated by the following examples in which all stated percentages are by weight unless otherwise indicated.

EXAMPLE 1

A solution of 127 grams (g) (1.0 mole) of 2,2-dichloropropionaldehyde, 106 g of acrylonitrile (2.0 mole), 3.0 g CuCl and 3.0 g of triphenylphosphine and CH₃CN (500 ml) was charged into the feed reservoir of a continuous reactor.

A reactor coil, constructed from ¼ inch O.D. nickel tubing, having a volume of 30 ml, was charged with acetonitrile, pressurized to 250 psi with dry N₂ and immersed in an oil bath preheated to 195° C. The reaction solution was pumped into the coil at a rate of 1.5 cc/min. The reaction mixture was then passed through a heat exchanger and collected in a blowdown chamber. Upon completion of the feed addition the coil was flushed through with acetonitrile. Analysis of the reaction mixture showed a 38% conversion of 2,2-dichloropropionaldehyde with a 94.9% selectivity to 5-oxo-2,4-dichloro-4-methylpentanenitrile, observed as a 1:1 mixture of diastereomers, and 2,3-dichloro-5-methylpyridine. The ratio of pyridine to oxonitrile was 1.76 to 1. No tars were found.

The above experiment was repeated except to use reactors made of different materials as specified below. The conversions and yields, based on consumed dichloropropionaldehyde, are also given.

| Reactor Material | Conversion % | Yield % Nitrile | Yield % Pyridine |
|---|---|---|---|
| Steel | 75 | ~0.5 | 4.45 |
| Stainless Steel | 25 | 30 | 33 |
| Hastalloy C | 40 | 40 | 15 |
| Monel 400 | 42 | 77 | 3 |
| Ni 200* | 20 | 94 | — |
| Ni 200 | 38 | 44 | 56 |

*a 13 minute run at 2.3 ml/min.

EXAMPLE 2

A solution of 14.1 g (0.1 mole) of 2,2-dichlorobutyraldehyde, 10.6 g (0.2 mole) of acrylonitrile, 0.3 g CuCl and 0.3 g triphenylphosphine was charged into the feed reservoir of the continuous reactor described in Example 1. The coil was pressurized to 250 psi with dry N₂ and preheated to 195° C. The reaction solution was pumped into the coil at the rate of 15 cc/min and then passed through a heat exchanger and collected in a blowdown chamber. Upon completion of the feed addition, the coil was flushed with 3 volumes of acetonitrile. Analysis of the reaction mixture by G.C. showed a 24% conversion with 87% selectivity to 5-oxo-2,4-dichloro-4-ethylpentane nitrile, observed as an equimolar mixture of diastereomers, and 2,3-dichloro-4-ethyl pyridine. The ratio of oxonitrile to pyridine was 12.5:1.

Unreacted starting materials and solvent were removed from the reaction mixture in vacuo by means of a rotary evaporator and the residue was distilled through a Kugelrohr apparatus (130° C., 0.3 mmHg) to afford 4.2 g of oxonitrile and 0.4 g of pyridine.

| NMR Oxonitrile (Acetone d$_6$) | | NMR Pyridine (Acetone d$_6$) | |
|---|---|---|---|
| $\delta$(TMS) | 1.00 (t) | | 1.20 (t) |
| | 1.75-2.3 (m) | | 2.20 (q) |
| | 2.5-3.3 (m) | | 7.75 (d) |
| | 5.09 (t) | | 8.20 (d) |
| | 9.55 (s) | | |
| $^{13}$CNMR of Diastereomeric Oxonitriles (Acetone d$_6$) | | | |
| $\delta$(TMS) | 196.56 | CHO | |
| | 195.80 | | |
| | 117.98 | CN | |
| | 76.63 | CH$_2$ Cl | |
| | 76.10 | \\ / | |
| | | C | |
| | | / \\ | |
| | 43.41 | Cl   Cl | |
| | 42.73 | \|    \| | |
| | | C—CH$_2$—C | |
| | 40.31 | | |
| | 39.73 | \| | |
| | | —CHCl | |
| | 32.23 | —CH$_2$—CH$_3$ | |
| | 31.40 | | |
| | 8.80 | CH$_3$ | |
| $^{13}$CNMR Pyridine (Acetone d$_6$) | | | |
| $\delta$(TMS): | | | |
| 147.50, 145.57, 140.77, 138.76, 129.36 ring carbons; | | | |
| 24.67, 14.93 ethyl group carbons | | | |

Various modifications may be made in the present invention without departing from the spirit or scope thereof and it is understood that we limit ourselves only as defined in the appended claims.

What is claimed is:

1. A continuous process for making compounds having the formula

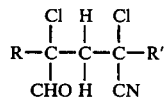

where R and R' are individually hydrogen or a straight or branched chain aliphatic radical having 1 to 8 carbon atoms, phenyl, benzyl, cyclohexyl, trichloro or trifluoromethyl which comprises reacting an aldehyde having the formula

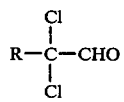

where R is as above-defined, with an acrylonitrile compound having the formula

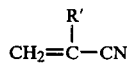

where R' is as defined above in the presence of a transition metal catalyst in a continuous reactor having an interior surface constructed of materials containing no more than a minor percentage of iron.

2. Process of claim 1 where R is methyl and R' is hydrogen.

3. Process of claim 1 wherein the reaction is carried out at a temperature of 95° to 220° C.

4. Process of claim 3 wherein the catalyst is CuCl.

5. Process of claim 4 wherein triphenylphosphine is employed as a co-catalyst.

6. Process of claim 1 wherein the mole ratio of dichloroaldehyde to acrylonitrile compound is from 1:1 to 1:3.

7. Process of claim 1 wherein the reactor is made of material containing nickel.

* * * * *